United States Patent
Butterworth

(10) Patent No.: US 8,684,944 B2
(45) Date of Patent: Apr. 1, 2014

(54) THERMOMETER

(75) Inventor: Andrew Butterworth, N. Somerset (GB)

(73) Assignee: University of Bristol, Bristol (GB)

( * ) Notice: Subject to any disclaimer, the term of this patent is extended or adjusted under 35 U.S.C. 154(b) by 314 days.

(21) Appl. No.: 10/507,931

(22) PCT Filed: Mar. 14, 2003

(86) PCT No.: PCT/GB03/01144
§ 371 (c)(1),
(2), (4) Date: Apr. 28, 2005

(87) PCT Pub. No.: WO03/078949
PCT Pub. Date: Sep. 25, 2003

(65) Prior Publication Data
US 2005/0192512 A1    Sep. 1, 2005

(30) Foreign Application Priority Data
Mar. 16, 2002 (GB) .................................. 0206260.2

(51) Int. Cl.
*A61B 5/00* (2006.01)
(52) U.S. Cl.
USPC ........................................................ 600/549
(58) Field of Classification Search
USPC ......... 600/551, 549, 300, 304, 372, 373, 587, 600/588
See application file for complete search history.

(56) References Cited

U.S. PATENT DOCUMENTS

| | | | | |
|---|---|---|---|---|
| 3,274,994 A | * | 9/1966 | Sturm | 600/549 |
| 3,583,389 A | * | 6/1971 | Harvey | 600/549 |
| 3,889,658 A | * | 6/1975 | Newhall | 600/549 |
| 3,895,523 A | * | 7/1975 | Nollen | 374/162 |
| 4,090,504 A | * | 5/1978 | Nathan | 600/483 |
| 4,151,831 A | * | 5/1979 | Lester | 600/549 |
| 4,154,106 A | * | 5/1979 | Inoue et al. | 374/104 |
| 4,248,089 A | * | 2/1981 | Heinmets | 374/162 |
| 4,333,477 A | | 6/1982 | Chervitz | |
| 4,345,470 A | * | 8/1982 | Hof et al. | 374/106 |
| 4,502,487 A | | 3/1985 | DuBrucq et al. | |
| 4,515,167 A | * | 5/1985 | Hochman | 600/549 |
| 4,651,137 A | * | 3/1987 | Zartman | 340/573.3 |
| 4,676,254 A | * | 6/1987 | Frohn | 600/549 |
| 4,844,076 A | * | 7/1989 | Lesho et al. | 600/302 |
| 5,137,028 A | * | 8/1992 | Nishimura | 600/551 |
| 5,209,238 A | * | 5/1993 | Sundhar | 600/551 |
| 5,482,373 A | * | 1/1996 | Hutchinson | 374/141 |
| 5,499,631 A | * | 3/1996 | Weiland | 600/547 |
| 5,991,700 A | | 11/1999 | Clay et al. | |
| 6,080,118 A | * | 6/2000 | Blythe | 600/591 |
| 6,169,914 B1 | * | 1/2001 | Hovland et al. | 600/340 |

(Continued)

FOREIGN PATENT DOCUMENTS

| | | |
|---|---|---|
| DE | 4122930 A | 2/1992 |
| EP | 0090327 A | 10/1983 |

(Continued)

*Primary Examiner* — Max Hindenburg
(74) *Attorney, Agent, or Firm* — Bozicevic, Field & Francis LLP; Bret E. Field

(57) ABSTRACT

A thermometer is described which is suitable as an indwelling thermometer to detect pyrexia or oestrus in a mammal. The thermometer provides a continued signal that a predetermined reference temperature has been exceeded, which temperature is selected to be indicative of pyrexia or oestrus in a given species and may change according to species.

30 Claims, 1 Drawing Sheet

(56) References Cited

U.S. PATENT DOCUMENTS

Figure 1A:
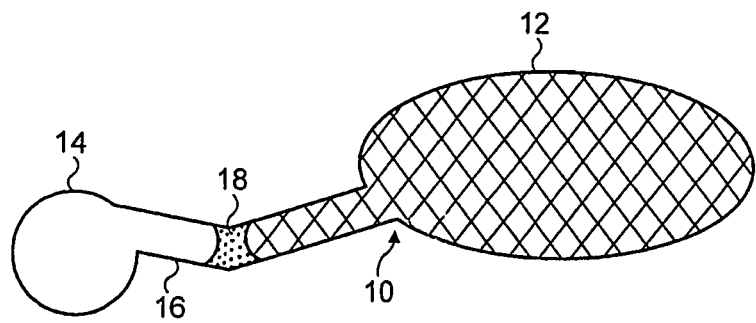

| | | | |
|---|---|---|---|
| 6,544,614 B1 * | 4/2003 | Huffer et al. | 428/40.1 |
| 2002/0010390 A1 * | 1/2002 | Guice et al. | 600/300 |
| 2003/0022392 A1 * | 1/2003 | Hudak | 436/518 |
| 2003/0083590 A1 * | 5/2003 | Hochman et al. | 600/549 |

FOREIGN PATENT DOCUMENTS

| | | |
|---|---|---|
| EP | 0167262 A | 1/1986 |
| JP | 11316161 A | 11/1999 |
| JP | 2000005136 A | 8/2000 |

* cited by examiner

THERMOMETER

This invention relates to a thermometer. More particularly, the present invention relates to an indwelling thermometer for clinical use.

Thermometers are well known in the art for providing an indication of temperature. Generally, thermometers comprise a heat-expandable fluid which is constrained to flow in a tube with indicia printed on the tube along the direction of expansion of the fluid; in use, the temperature is determined by reading the indication adjacent the leading edge of the fluid in the tube.

Recently, digital thermometers have been developed where a temperature is determined electronically and a digital indication of the temperature is provided.

More recently, disposable thermometers have been produced where the temperature indication is given using thermochromatic inks for predetermined reference intervals, an approximate temperature being provided by noting which inks have changed colour and which temperature they correlate to.

The present invention concerns an indwelling thermometer. In the description which follows the term "indwelling" is intended to define a thermometer which is left in a predetermined place for a long period of time to indicate that a rise in temperature above a predetermined threshold has occurred.

The invention will be described with particular reference to its preferred application in monitoring the temperature of the mammalian body, however, the invention finds equal utility in other areas where it is desirable to indicate that an unacceptable rise in temperature has occurred, for example in storage areas where spoilage may occur if a given temperature is exceeded.

In mammals a rise in temperature, especially in core body temperature, may be taken to be an indication of the presence of a pathology or of an infection. An early indication of infection can be vitally important to a farmer where the infection might spread through a herd of animals and early detection may prevent the spread of infection or unnecessary slaughter of uninfected animals.

In female mammals a temperature rise may also be indicative of ovulation or that oestrus is about to occur in mammals where actual release of the ovum is triggered by penetration. Both of these events are of interest to a farmer, a veterinary or medical practitioner and a woman experiencing difficulties in trying to conceive.

It is therefore an object of the present invention to provides a device which provides a signal that a rise in temperature above a predetermined threshold has occurred.

Accordingly, the present invention provides an indwelling thermometer comprising temperature sensing means and signal means for providing a continued indication that a predetermined threshold temperature has been exceeded.

Advantageously, the provision of a continued signal that the predetermined temperature has been exceeded enables the viewer to establish that the temperature has in fact been exceeded without continual monitoring of the subject. By the term "Continued Signal" as used herein is intended a signal which keeps signalling and does not stop signalling.

It is a further object of the invention to provide means for establishing that predetermined threshold temperature. Advantageously, this allows for temperature profiles of an individual subject to be established and used to eliminate minor temperature variations due to external temperature, exercise or sleep.

The signal means may provide a visual, aural, or mechanical indication that the temperature has been exceeded. For example, the signal may be the movement of an indicator device, the illumination/quenching of a light, the release of a marker dye, colour change of a thermochromatic ink, vibration of the thermometer, generation of a radio signal, activation of a buzzer or alarm, or an analogue or a digital telemetry system signal.

The temperature sensing means may be electronic, chemical or mechanical. For example the temperature sensing means may be a thermochromatic dye, a wax or grease with a specific melting point, a thermodeformable plastics material, a thermocouple linkage, a thermistor or a printed circuit board.

The thermometer preferably dwells in a body cavity of the subject mammal, for example, the ear cavity or the vagina. Temperatures that are measured in the ear cavity tend to be very accurate since the ear cavity is so close to the brain. However, the thermometer may also be wholly or partially implanted into a subject mammal, for example, it may be implanted beneath the skin.

It is intended that in it's most simple form the thermometer of the invention gives, an indication that the threshold has been exceeded, however, in an alternative embodiment, the invention also provides means for recording the temperature of the subject over a predetermined period of time.

Preferably, the thermometer comprises a biocompatible material. By the term "biocompatible material" as used herein is intended a material which is suitable for leaving in situ in a subject animal for a long period of time without causing irritation, tissue growth, infection or promoting infection or an immunological, including autoimmunological, reaction. The thermometer of the invention may be made of or coated with such a material. Examples of such materials include surgical grade polymers, such as:

ABS—acrylonitrile-butadiene-styrene terpolymer
COPE—copolyester elastomer
EAA—ethylene acrylic acid
EMA—ethylene methylacrylate
EVA—ethylene-vinyl-acetate
HDPE—high-density polyethylene
HIPS—high-impact polystyrene
LCP—liquid crystal polymer
LDPE—low-density polyethylene
LLDPE—linear low-density polyethylene
PBT—poly(butylene terephthalate)
PC—polycarbonate
PC/ABS—polycarbonate-ABS alloy/blend
PC/PET—polycarbonate-PET alloy/blend
PE—polyethylene
PEI—polyetherimide
PET—poly(ethylene terephthalate)
PP—polypropylene
PPO—poly(phenylene oxide)
PUR—polyurethane
PVC—polyvinyl chloride
SAN—styrene acrylonitrile
SBC—styrene block copolymer
SPS—syndiotactic polystyrene
TPE—thermoplastic elastomer
TPO—thermoplastic olefin
TPU—thermoplastic urethane
ULDPE—ultra low-density polyethylene
VLDPE—very low-density polyethylene
Silicone
Biodegradable Copolymers
Copolymer Coatings
Pseudo—Poly(Amino-Acids)

Ceramic Composites
Thermoplastic-Fiber Composites
PYROLYTIC CARBON Pyrolite

In a first embodiment, the invention simply provides an indication that the predetermined threshold temperature has been exceeded. The thermometer is preferably in the form of an enclosed hollow container comprising two chambers separated by a waisted portion of the container. The container is preferably formed from a biocompatible material. The waisted portion of the container preferably contains the temperature sensing means while one of the chambers contains the signal means.

In this embodiment the temperature sensing means is a wax or grease, the melting point of which is at or close to the predetermined threshold temperature, and the signal means is preferably a marker dye contained in one chamber of the container only. Preferably, the wax or grease forms a plug in the waisted portion of the container such that the movement of the marker dye between the chambers of the container is prevented.

Examples of waxes or greases which may be used in the present invention include beeswax, lanolin, petroleum jelly, white petrolatum, spermaceti, cocoa butter, stearic acid, glycerinated gelatin, candelila wax, carnauba wax, or mixtures of any of these with oils such as sweet almond oil, liquid paraffin or any vegetable oil, especially hydrogenated vegetable oils, fatty acids or polyethylene glycol (PEG).

Compounds or mixtures which melt at or close to body temperature are widely known in the art in the formation of suppositories, pessaries or some emollients, cosmetics or moisturisers such as lip balms or lipsticks. Hence, the person skilled in the art could readily select a proprietary suppository base formulation for use as the wax or grease of this embodiment of the present invention. For example, a range of suppository bases which melt at temperatures of between 33 and 44° C. and are available under the trade name DUB-PP from Stearinerie-Dubois of France, could be used in the present invention.

In use, the thermometer is applied to the animal in a manner such that the chamber containing the marker dye is held internally in the animal while the other chamber is external of the animal and is visible, when the predetermined threshold temperature is exceeded, the wax or grease melts and allows travel of the marker dye to the visible chamber.

Preferably, the container is shaped such that the melted wax or grease, when cooled, cannot re-plug the waisted portion of the container, for example the regions adjacent the waisted portion may flare outwardly. Alternatively, the thermometer may be introduced to the subject mammal in a manner such that the chamber holding the marker dye is above the plug and the second, empty chamber hence, when the plug melts, the melted wax or grease will drain into the lower second chamber with the marker dye thereby preventing the waisted portion from becoming resealed.

The overall shape of the container is not critical although it is preferred that the thermometer does not cause discomfort to the subject mammal and in this respect it is preferred that the container is rounded or elliptical or other shape which does not present undue trauma to the animal. Ideally, the thermometer is shaped such that it is not likely to be easily lost if it is inserted into a body cavity such as the ear or the vagina. Additionally, where appropriate, it is desirable that the chambers are of unequal size to ensure that sufficient marker dye for detection is transferred from one chamber to the other.

The waisted portion of the thermometer may be a slight waisting of the container or, for more rapid melting of the wax or grease which may be held therein, be a narrow waisting or venturi. Ideally, the waisted portion is a tube of narrow cross-section with respect to the chambers, especially in the above-described embodiment where the temperature sensing means is a wax of grease which melts to allow transfer of a marker dye from one chamber to the other.

In order to establish the predetermined reference temperature the invention also provides a kit of thermometers, each thermometer detecting a different specific temperature, whereby in use a user applies a different thermometer to a subject animal each day to establish the range of normal temperature variation throughout a day for that subject animal. When used in this way, the kit provides an indication of the normal temperature range for that animal and allows selection of a thermometer indicating a temperature above the maximum daily variation for the detection of infection or of ovulation.

Alternatively, the predetermined reference temperature can be determined using an electronic temperature recording device which is introduced to and left to dwell in the subject mammal for a period of time, for example one week or one month, to record the temperature of the individual at selected intervals over that period of time, for example every 20 minutes for one week. An example of a device suitable for this purpose is the device sold under the trade name "Tiny Talk"™ from RS Components Ltd., modified to be smaller and to have sufficient battery power to record the temperature variations for the required length of time.

In a second embodiment, the thermometer of the present invention is an electronic device in which the temperature sensing means comprise a thermistor and the signal means provide an optical or audible signal.

Preferably, the temperature sensing means comprise a thermistor set at or close to the predetermined threshold temperature. Alternatively, a bimetallic strip or a printed circuit board or a proprietary device such as those sold under the trade names Tiny tag Transit, Therma Tag or Button having been modified to provide a continued signal and to be indwelling may be used to sense the temperature.

In order to ensure that the signal means continues to provide a signal even when the temperature subsequently drops below the reference temperature, the thermometer may further comprise means to prevent cancellation of the signal. Preferably, the cancellation prevention means comprises a latch. The latch may be a diode, a digital to analogue converter, an integrated circuit or a digital latch.

Preferably, the signal means provide a light output, for example the illumination or extinguishing of an LED or other light source, or a sound output such as the activation of a buzzer, beep or other alarm sound. The activation of the signal is preferably irreversible ensuring that the increased temperature is detected. Alternatively, the signal means may be a radio transmitter which sends a signal to a remote receiving station, the alarm signal being generated at the receiving station. The signal means may also send a mobile telecommunications signal to a mobile telephone, for example in the form of a "text" or SMS message or as a pre-recorded voice message. This allows for remote telemetry monitoring of, for example, a herd of cows or sheep.

In this embodiment, it is also desirable to provide means for recording the temperatures sensed by the temperature sensing means. This data may be stored on a memory chip or other data storage device. The data storage may be remote, especially where the signal is sent to a remote receiving station, or can be contained within the device.

Additionally, a computer program may be used where the program compares the data contained within the signal to stored data, the program may then vary or set the predetermined temperature, for example by means of a discriminating function. In this way, the program can make a decision, based on the received data when compared to the stored data.

In a third embodiment, the thermometer may be formed from a plastics material with a thermochromatic pigment or ink incorporated therein. In this embodiment the temperature sensing means and the signal means may both be the thermochromatic pigment or ink, or the temperature sensing means may be the thermochromatic pigment or ink, and the signal means may be fixative to prevent the thermochromatic pigment or ink reverting to its original colour.

The predetermined reference temperature is likely to be in the region of 35-44° C., preferably approximately 39° C., since mammalian core temperature is generally in the region of 37-38° C. Examples of normal core body temperatures are as follows:—

| Animal | ° C. |
|---|---|
| Dog | 38.9 |
| Cat | 38.6 |
| Stallion | 37.6 |
| Mare | 37.8 |
| Rabbit | 39.5 |
| Pig | 39.2 |
| Goat | 39.1 |
| Sheep | 39.1 |
| Dairy cow | 38.6 |
| Human | 37.3 |

Hence, the pre-determined reference temperature which is considered to be indicative of infection or of oestrus will be modified according to which mammal the thermometer will be used with.

Additionally, the size and shape of the thermometer can be adapted according to the subject mammal it is to be used in.

Where a visual signal is generated, it is preferable that the externally oriented portion of the thermometer be sufficiently large to be readily seen. For example, in farm animals the thermometer is likely to be read by a farmer when inspecting the cows, such as at milking time. In sheep, the externally oriented portion of the device may be sized so that it can be detected from a distance when herding the sheep. When to be used in the human female it is preferable that the device be shaped and sized similar to a tampon for comfort and ease of use for the user.

Figure 1B:
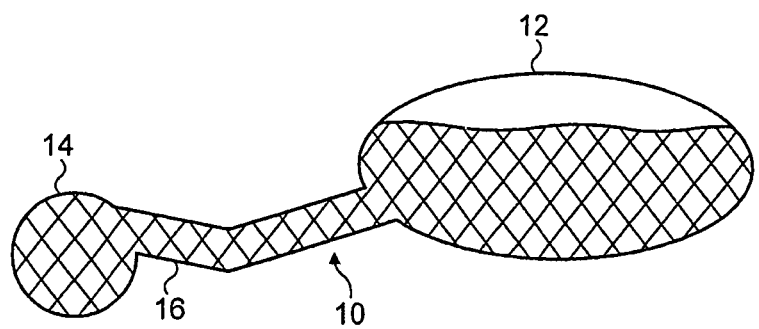
Figure 2:
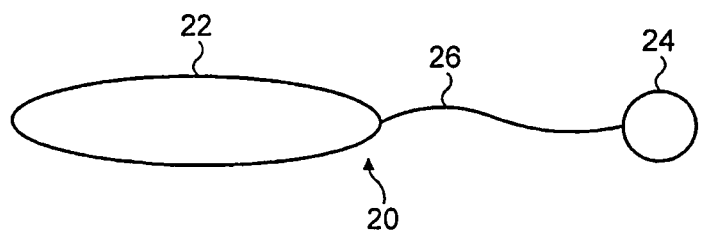

Embodiments of the invention will now be described, by way of example only, with reference to the accompanying drawing of which, FIGS. 1a and 1b show a first embodiment of the thermometer of the invention, and FIG. 2 is a schematic representation of an electronic version of the thermometer of the present invention.

Referring to FIG. 1a a thermometer 10 is provided which is in the form of a container having two chambers 12 and 14 separated by a waisted portion 16. The waisted portion 16 is in the form of a narrow tube and contains a plug 18 of a wax having a melting temperature of 40° C. for use in dairy cows. The wax used is a standard suppository base wax, e.g. a mixture of stearic acid, cocoa butter and PEG. Chamber 12 contains a marker dye and is much larger than chamber 14 to ensure transfer of the marker dye to chamber 14 on removal, by melting, of the plug 18. The thermometer 10 is made from a medical grade plastics material.

FIG. 1b shows the thermometer 10 of FIG. 1a after the wax plug 18 has melted due to the increase in body temperature above the predetermined threshold temperature of 40° C.

Referring to FIG. 2 an electronic version 20 of the device is shown. The device 20 comprises a sensor 22. The sensor 22 may be a device such as that sold under the trade-name iButton modified to provide a continued signal and to be indwelling for example by being coated with a biocompatible or non-irritant material, linked to an indicator 24, in the form of an LED, by a conductor 26 also coated with a biocompatible or non-irritant material. A latch is interposed between sensor 22 and indicator 24 to prevent cancellation of the signal and thereby to ensure the continued illumination of indicator 24.

In use, the device is inserted into the vagina of a cow and left in place. When sensor 22 detects a rise in temperature above a predetermined threshold it sends a signal along connector 26 to indicator 24, which illuminates. On visual inspection, the farmer, or a vet, then knows that the temperature of that particular cow has exceeded the threshold temperature and can investigate pyrexia or oestrus in that animal.

In the human female, the present invention is primarily used for the detection of ovulation rather than to monitor for infection. However, it is still possible to use the invention to monitor infection in this way. It is also preferred that the present invention be usable without the need for a medical practitioner although use under medical supervision is not to be excluded.

In such a use it is intended that a device of the invention 10,20 is worn per vaginem continuously for at least one complete menstrual cycle so that the temperature peak experienced prior to ovulation can be determined and be distinguished from temperature fluctuations due to other causes.

In one embodiment for this application the user may use a series of disposable indwelling thermometers 10 each of which has a wax or grease 18 which is predetermined to melt at an incrementally higher temperature, for example one at 36.9° C., one at 37.1° C., one at 37.5° C. etc since normal human body temperature varies between 36.8 and 37.3° C., depending on the individual and on the level of activity being undertaken.

Once the normal temperature of the user has been established thermometers 10 are selected where the wax or grease 18 melts at the ovulation-indicative temperature rise. The thermometer 10 is worn continually until dye 12 can be seen in chamber 14, which is indicative of ovulation. Intercourse can then be timed to improve the chances of conception.

Using the second embodiment, the thermometer device 20, is again worn per vaginem to establish the normal body temperature range of the user. Devices 20 are used where the signaling threshold is varied. This can be done using one device 20 where the temperature threshold can be manually set or by using a series of pre-set, fixed temperature devices. Again, the device 20 is left in place throughout a complete menstrual cycle to establish the ovulation-indicative temperature peak of the user. Then, either the device 20, is set to be at or just below the desired temperature or a device 20 is selected which has a fixed predetermined temperature and operates at or just below the ovulation-indicative temperature of the user.

The invention claimed is:

1. A vaginal indwelling thermometer for use in a vagina of a subject mammal, the thermometer comprising:
    a housing comprising:
        a temperature sensing means which generates data indicative of the per vaginem temperature of the subject mammal;
        a temperature recording means integral with the temperature sensing means, wherein the temperature recording means records temperature data generated by the temperature sensing means; and a wired data connection port, wherein the vaginal indwelling thermometer has a shape that does not cause undue trauma to said subject mammal and is configured to be positioned in and left in said vagina of said subject mammal continuously for at least one week.

2. An indwelling thermometer according to claim 1, wherein the temperature sensing means is an electronic, chemical or mechanical temperature sensing means.

3. An indwelling thermometer according to claim 1, wherein the temperature sensing means comprises a thermocouple linkage or a thermistor.

4. An indwelling thermometer according to claim 1, wherein the housing comprises a biocompatible material.

5. An indwelling thermometer according to claim 4, wherein the housing is formed from a material selected from the group consisting of acrylonitrile-butadiene-styrene terpolymer, copolyester elastomer, ethylene acrylic acid, ethylene methylacrylate, ethylene-vinyl-acetate, high-density polyethylene, high-impact polystyrene, liquid crystal polymer, low-density polyethylene, linear low-density polyethylene, poly(butylene terephthalate), polycarbonate, polycarbonate, alloy/blend, polycarbonate-PET alloy/blend, polyethylene, polyetherimide, poly(ethylene terephthalate), polypropylene, poly(phenylene oxide), polyurethane, polyvinyl chloride, styrene acrylonitrile, styrene block copolymer, syndiotactic polystyrene, thermoplastic elastomer, thermoplastic olefin, thermoplastic urethane, ultra low-density polyethylene, very low-density polyethylene, silicone, biodegradable copolymers, copolymer coatings, pseudo-poly(amino-acids), ceramic composites, thermoplastic-fiber composites, pyrolytic carbon and pyrolite.

6. An indwelling thermometer according to claim 1, wherein the temperature sensing means is configured to record data every 20 minutes.

7. An indwelling thermometer according to claim 1, wherein said subject mammal is human.

8. An indwelling thermometer according to claim 1, wherein the thermometer is configured to be worn per vaginem for at least one entire menstrual cycle.

9. An indwelling thermometer according to claim 4, wherein the thermometer is configured to be used to determine ovulation in the subject mammal.

10. A device for predicting ovulation in a subject mammal, the device comprising:
a housing having a shape that does not cause undue trauma to said subject mammal and configured to be positioned in and left in a vagina of said subject mammal for at least one week;
a temperature sensing means located within said housing for generating data indicative of the per vaginem temperature of the subject mammal;
a temperature recording means located within the housing which records the temperature data generated by the temperature sensing means; and
a wired data connection port.

11. A device according to claim 10, wherein said temperature sensing means is an electronic, chemical or mechanical temperature sensing means.

12. A device according to claim 10, wherein said temperature sensing means comprises a thermocouple linkage or a thermistor.

13. A device according to claim 10, wherein said subject mammal is human.

14. A device according to claim 10, wherein said housing comprises a biocompatible material.

15. A device according to claim 14, wherein said housing is formed from a material selected from the group consisting of acrylonitrile-butadiene-styrene terpolymer, copolyester elastomer, ethylene acrylic acid, ethylene methylacrylate, ethylene-vinyl-acetate, high-density polyethylene, high-impact polystyrene, liquid crystal polymer, low-density polyethylene, linear low-density polyethylene, poly(butylene terephthalate), polycarbonate, polycarbonate, alloy/blend, polycarbonate-PET alloy/blend, polyethylene, polyetherimide, poly(ethylene terephthalate), polypropylene, poly(phenylene oxide), polyurethane, polyvinyl chloride, styrene acrylonitrile, styrene block copolymer, syndiotactic polystyrene, thermoplastic elastomer, thermoplastic olefin, thermoplastic urethane, ultra low-density polyethylene, very low-density polyethylene, silicone, biodegradable copolymers, copolymer coatings, pseudo-poly(amino-acids), ceramic composites, thermoplastic-fiber composites, pyrolytic carbon and pyrolite.

16. A device according to claim 10, wherein said temperature sensing means is configured to record data every 20 minutes.

17. The indwelling thermometer according to claim 1, further comprising a signaler configured to provide a continued signal.

18. The indwelling thermometer according to claim 17, wherein the signaler is selected from the group consisting of an indicator device, a light, a vibrator, a radio signal generator, a buzzer, an alarm and a telemetry system.

19. The device according to claim 10, further comprising a signaler configured to provide a continued signal.

20. The device according to claim 19, wherein the signaler is selected from the group consisting of an indicator device, a light, a vibrator, a radio signal generator, a buzzer, an alarm and a telemetry system.

21. The indwelling thermometer according to claim 1, wherein the thermometer has a rounded or elliptical shape.

22. The device according to claim 10, wherein the housing has a rounded or elliptical shape.

23. A vaginal indwelling thermometer for use in a vagina of a subject mammal, the thermometer comprising:
a housing comprising:
a temperature sensing means configured to generate data indicative of the per vaginem temperature of the subject mammal;
a temperature recording means integral with the temperature sensing means and configured to record temperature data generated by the temperature sensing means; and
a wired data connection port; and
a removal means,
wherein the vaginal indwelling thermometer has a shape that does not cause undue trauma to said vagina of said subject mammal,
wherein said housing is configured to be contained within said vagina of said mammal to provide said per vaginem temperature, and
wherein said vaginal indwelling thermometer is configured to be positioned in and left in said vagina of said subject mammal continuously overnight.

24. An indwelling thermometer according to claim 23, wherein the temperature sensing means is an electronic, chemical or mechanical temperature sensing means.

25. An indwelling thermometer according to claim 23, wherein the temperature sensing means comprises a thermocouple linkage or a thermistor.

26. An indwelling thermometer according to claim 23, wherein the housing comprises a biocompatible material.

27. An indwelling thermometer according to claim 26, wherein the housing is formed from a material selected from the group consisting of acrylonitrile-butadiene-styrene terpolymer, copolyester elastomer, ethylene acrylic acid, ethylene methylacrylate, ethylene-vinyl-acetate, high-density polyethylene, high-impact polystyrene, liquid crystal polymer, low-density polyethylene, linear low-density polyethylene, poly(butylene terephthalate), polycarbonate, polycarbonate, alloy/blend, polycarbonate-PET alloy/blend, polyethylene, polyetherimide, poly(ethylene terephthalate), polypropylene, poly(phenylene oxide), polyurethane, polyvinyl chloride, styrene acrylonitrile, styrene block copolymer, syndiotactic polystyrene, thermoplastic elastomer, thermoplastic olefin, thermoplastic urethane, ultra low-density polyethylene, very low-density polyethylene, silicone, biodegradable copolymers, copolymer coatings, pseudo-poly (amino-acids), ceramic composites, thermoplastic-fiber composites, pyrolytic carbon and pyrolite.

28. An indwelling thermometer according to claim 23, wherein the temperature sensing means is configured to record data every 20 minutes.

29. An indwelling thermometer according to claim 23, wherein said subject mammal is human.

30. An indwelling thermometer according to claim 23, wherein the thermometer is configured to be used to determine ovulation in the subject mammal.

* * * * *